United States Patent [19]

Harvey et al.

[11] Patent Number: 4,816,221
[45] Date of Patent: Mar. 28, 1989

[54] METHOD OF SIMULTANEOUSLY ASSEMBLING AND STERILIZING A UNITARY CONTAINER AND A FLUID TRANSFER SET

[75] Inventors: Roger W. Harvey, Vernon Hills; William J. Schnell, Libertyville, both of Ill.

[73] Assignee: Baxter Travenol Laboratories, Inc., Deerfield, Ill.

[21] Appl. No.: 939,374

[22] Filed: Dec. 8, 1986

[51] Int. Cl.⁴ .............................................. A61L 31/00
[52] U.S. Cl. .................................. 422/25; 422/26; 422/38; 156/281; 156/294; 604/283; 604/905
[58] Field of Search ............................ 422/25, 26, 38; 604/905, 283; 156/294, 281

[56] References Cited

U.S. PATENT DOCUMENTS

| | | | |
|---|---|---|---|
| 3,058,799 | 10/1962 | Rowles, Jr. | 422/26 |
| 4,157,723 | 1/1979 | Granzow et al. | 604/905 |
| 4,195,632 | 4/1980 | Parker et al. | 604/905 |
| 4,265,280 | 5/1981 | Granzow et al. | 604/905 |
| 4,369,779 | 1/1983 | Spencer | 604/905 |
| 4,376,051 | 3/1983 | Isono | 422/25 |
| 4,411,866 | 10/1983 | Kanno | 422/25 |
| 4,417,753 | 11/1983 | Bacehowski et al. | 156/294 X |
| 4,443,215 | 4/1984 | Smith | 604/905 |
| 4,610,670 | 9/1986 | Spencer | 604/905 |
| 4,619,642 | 10/1986 | Spencer | 604/905 |

Primary Examiner—Barry S. Richman
Assistant Examiner—Timothy M. McMahon
Attorney, Agent, or Firm—Paul C. Flattery; Daniel D. Ryan; Charles R. Mattenson

[57] ABSTRACT

A method of forming a unitary, sterile fluid dispensing assembly includes forming a fluid-filled container with a vinyl disposing port and forming a fluid transfer set with a vinyl spike connector. The spike connector is inserted into the vinyl disposing port thereby placing the set in fluid flow communication with the fluid in the container. The assembly is sterilized in an autoclave. The heat of sterilization melds at least a surface portion of the vinyl spike connector and softens an interior adjacent surface portion of the port on the container. After sterilization, the transfer set is permanently bonded to the container. The presence of the fluid in the transfer set during sterilization prevents fusing and closing of the lumens of the set due to the heat of sterilization.

1 Claim, 2 Drawing Sheets

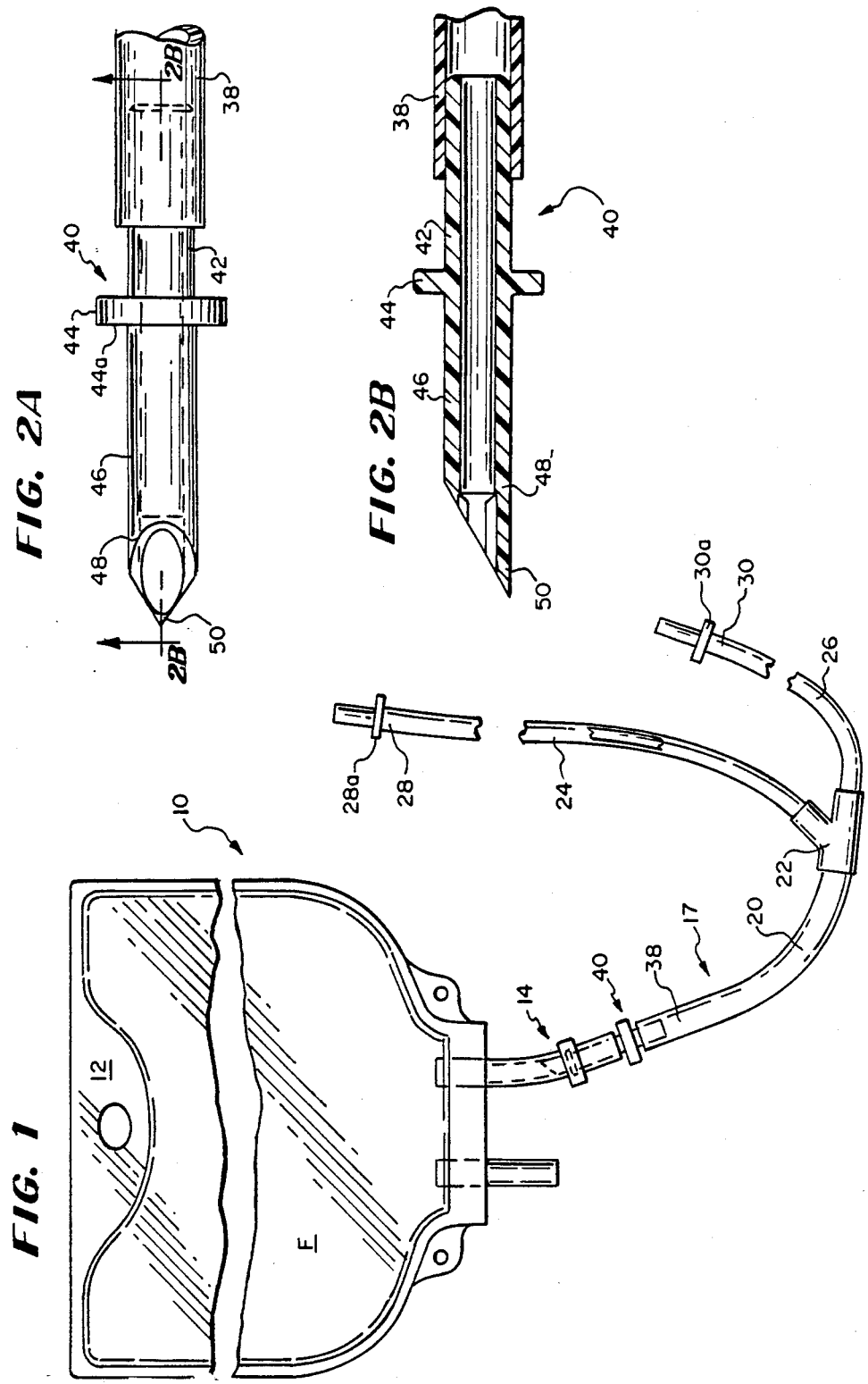

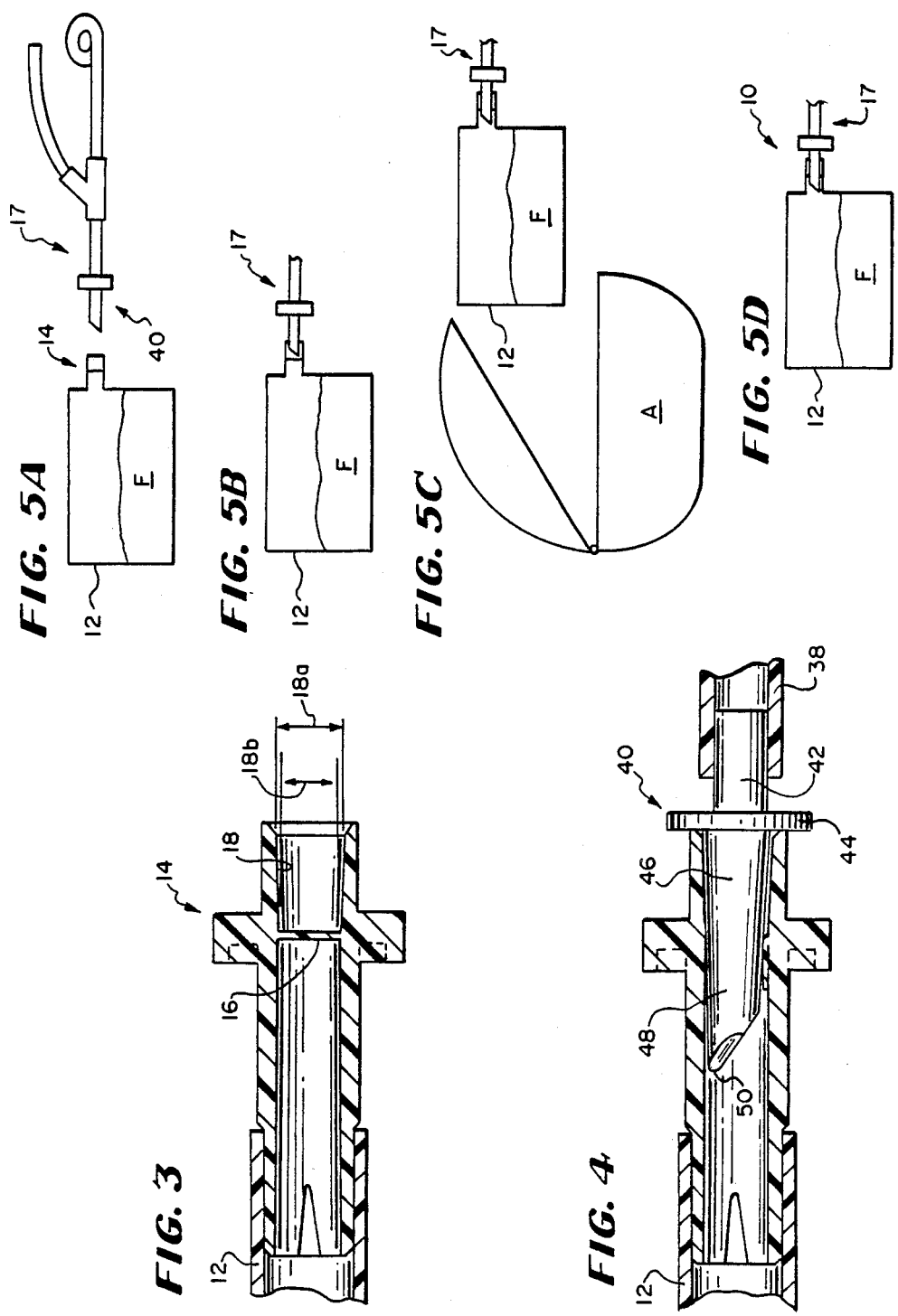

METHOD OF SIMULTANEOUSLY ASSEMBLING AND STERILIZING A UNITARY CONTAINER AND A FLUID TRANSFER SET

FIELD OF THE INVENTION

The invention pertains to an apparatus for dispensing various types of medically related fluids as well as sterilization of same. More particularly, the invention pertains to a method of sterilizing a fluid-filled container and attached fluid transfer set simultaneously while permanently fusing the transfer set to the container.

BACKGROUND OF THE INVENTION

The use of flexible containers filled with sterile fluids is generally known in the art. Further, the manufacture and use of sterile transfer sets which can be coupled to the flexible containers, usually via a dispensing port, are also generally known in the art.

Such fluid-filled containers and related transfer sets are routinely used for a variety of medically-related procedures. These include, dispensing of blood components, and dispensing and receiving peritoneal dialysis fluid. Further, the dispensing of various types of nutritional, parenteral and other medicinal solutions is well known.

The prior art transfer sets have often been formed of a medical grade vinyl plastic. The solution filled containers are often sterilized using steam sterilization in an autoclave. However, because of a tendency of the interior surfaces of the lumens of the transfer sets to soften and stick together, thereby blocking the fluid flow passages, such sets have not been routinely sterilized using heat. Rather, the transfer sets have very often been sterilized by means of radiation or gas.

It has also been generally known in the art to permanently couple the transfer sets to the fluid dispensing port of the container by means of a plastic softening solvent. The solvent bonds a selected connector or end of the lumen of the transfer set to the dispensing port on the container. There are circumstances where it is undesirable or not feasible to use solvent to bond these two members together. This is particularly the case where it is desirable to make sure that no solvent or solvent residue can be transferred to the fluid in the container.

Thus, there continues to be a need for a method of coupling a transfer set to a fluid-filled container which does not utilize known solvents. Further, there continues to be a need for sterile transfer sets coupled to fluid-filled containers where the sterilization of the container, the fluid and the transfer set has been carried out in a single step.

SUMMARY OF THE INVENTION

In accordance with the invention, a method is provided for attaching a fluid dispensing set to a fluid-filled container simultaneously while sterilizing the container, the set and the fluid. A fluid-filled container is provided. The container has a sealed, cylindrical fluid dispensing port. The fluid delivery set is sealed with the exception of a cylindrical spike connector attached to one of the tubular members of the set.

The spike connector has a fluid flow pathway therethrough. The spike connector is thus in fluid flow communication with the interior lumens of the transfer set.

The spike connector can be inserted into the dispensing port. A pointed end of the spike connector pierces the membrane seal in the port. Part of the fluid in the container flows into the sealed set.

In a preferred embodiment, the spike connector is formed of rigid, vinyl plastic with a softening point on the order of the temperatures achievable in an autoclave. The container and set can then be placed in an autoclave and sterilized. In the process, the fluid is also sterilized. The part of the fluid that flowed into the lumens of the set assists in sterilization of the set. In addition, that portion of the fluid in the lumens of the set keeps the fluid flow pathways open and prevents the interior walls of the lumens from sticking together and blocking fluid flow through the set.

When the container and set are sterilized, the sterilizing heat melds the exterior peripheral surface of the spike connector to the interior surface of the port. The connector and port fuse together. On cooling, the vinyl connector and port harden into a single unit.

The method is advantageous in that the container, fluid and set can be manufactured in non-sterile conditions, assembled and then sterilized as an integral unit. In addition, since the seal between the port and connector is formed as a result of sterilization heat, no solvent is used to create the seal. Hence, there will be no residual traces of solvent present to leach into the fluid in the container. Finally, the present method is advantageous in that only one type sterilization is needed for the set, the fluid and the container.

A particular advantage of the present method is that it can be used in conjunction with any fluid that can be sterilized by means of heat or autoclaving. Thus, the fluids can include dialysis, parenteral, nutritional or medicinal solutions.

Numerous other advantages and features of the present invention will become readily apparent from the following detailed description of the invention and the embodiments thereof, from the claims and from the accompanying drawings in which the details of the invention are fully and completely disclosed as a part of this specification.

DESCRIPTION OF THE DRAWINGS

FIG. 1 is an overall planar, schematic view of a flexible, fluid-filled container coupled to a fluid transfer set;

FIG. 2A is a top plan view of a spike connector in accordance with the present invention;

FIG. 2B is a side view, in section, taken along line 2B—2B of FIG. 2A;

FIG. 3 is a sectional view of the dispensing port of the fluid-filled container of FIG. 1;

FIG. 4 is a view, partly in section, illustrating the connector of FIG. 2 and an attached fluid transfer set coupled to the dispensing port of the container of FIG. 1; and FIGS. 5A through 5D illustrate schematically a method of assembling and sterilizing a container, fluid and a transfer set in accordance with the present invention.

DETAILED DESCRIPTION OF THE PREFERRED EMBODIMENT

While this invention is susceptible of embodiment in many different forms, there is shown in the drawing and will be described herein in detail a specific embodiment thereof with the understanding that the present disclosure is to be considered as an exemplification of the principles of the invention and is not intended to limit the invention to the specific embodiment illustrated.

FIG. 1 illustrates a fluid dispensing assembly 10 in accordance with the present invention. The assembly 10 includes a flexible plastic container 12 at least partly filled with a selected fluid F. The container 12 could be formed as is convention and well known in the art of any flexible, medical grade plastic. The fluid F contained within the container 12 can be any fluid which can be subjected to steam sterilization in an autoclave. Neither the exact shape nor composition of the container 12 nor the precise fluid F contained therein is a limitation of the present invention.

The container 12 is formed, as is well known in the art, with a dispensing port 14. The port 14 is sealed with a pierceable membrane 16, illustrated in FIG. 3, which retains the fluid F within the container 12. The port 14 is cylindrical with an interior peripheral surface 18 adjacent the membrane 16.

The fluid dispensing port 14 can be affixed to the container 12 in a variety of ways. For example, the port 14 can be sealed to the container 12 by means of radio frequency energy. The exact configuration of the port 14 and its manner of being sealed to the container 12 are not a limitation of the present invention. Preferably, the port 14 will be formed of a selected medical grade vinyl plastic.

Affixed to the container 12 and in fluid flow communication therewith is a fluid transfer set 17. The exemplary fluid transfer set 17, shown in FIG. 1, includes a first fluid flow conduit 20 coupled by a Y junction 22 to second and third fluid flow conduits 24 and 26. The conduits 20, 24 and 26 can be formed of conventional flexible medical grade plastic of a type that are well known in the art. Each of the conduits 24 and 26 has an end 28 and 30. Each of the ends 28 and 30 terminates in a dispensing port 28a and 30a. Each of the ports 28a and 30a is sealed by a pierceable membrane such as the membrane 16 in the port 14.

The conduit 20 has an end 38 with a spike connector 40 affixed thereto. The spike connector 40, illustrated in FIGS. 2A and 2B, slidably engages the port 14 of the bag 12 piercing the membrane 16 at the same time. Once the membrane 16 has been pierced, a portion of the fluid F in the container 12 can flow into the tubular members 20, 24 and 26 of the set 17. The membrane seals in the ports 28a and 30a prevent the portion of the fluid F therein from leaking from the set 17. As a result, the assembly 10 of FIG. 1 is a closed assembly which could be readily transported or delivered for subsequent use.

Access to the fluid F could be obtained using standard spike connectors to pierce the membranes in the ports 28a and 30a. It will be understood that the exact configuration of the fluid transfer set 17 is not a limitation of the present invention.

The connector 40, with respect to FIGS. 2A and 2B includes a cylindrical proximal end 42 on which is affixed the end 38 of the conduit 20. Adjacent the proximal cylindrical end 42 is an integrally-formed cylindrical flange 44. The flange 44 has a planar surface 44a located distally of the proximal end 42.

A cylindrical tapered member 46 is integrally-formed adjacent the surface 44a of the flange 44. The tapered member 46 terminates at a distal end 48 with a sharp point 50.

The point 50 is used for piercing the membrane 16 of the port 14. The spike connector 40 is hollow with an interior cylindrical peripheral wall 52 which defines a fluid flow path through the connector 40.

The substantially cylindrical interior surface 18 of the port 14, as illustrated in FIG. 3, has an end diameter 18a that is slightly larger than an interior diameter 18b adjacent the membrane 16. The surface 18 thus defines a frusto-conical shaped space into which the tapered distal end 46 of the spike connector 40 can be inserted.

The connector 40 when inserted into the port 14, as illustrated in FIG. 4, pierces the membrane 16. Part of the fluid F in the container 12 can then flow into the lumens of the tubular members 20, 24 and 26.

Subsequent to the connector 40 being inserted into the port 14, the assembly 10 can then be sterilized in an autoclave. The process of sterilization simultaneously bonds the connector 40 to the port 14.

The bonding or fusing occurs where the connector 40 has been molded of a rigid vinyl plastic having a relatively low melding point. With such a connector, and assuming the port 14 is formed of an appropriate vinyl material as well, when the assembly 10 is heated to sterilization temperatures, the tapered surface of the distal portion 46 of the connector 40 melds and fuses with the heat softened interior peripheral surface 18 of the port 14.

It is believed that plasticizers in the vinyl migrate when heated. This migration between the connector 40 and port 14 forms a fluid tight bond.

The presence of a portion of the solution F in the lumens 20, 24 and 26 assists in the sterilization process. In addition, that fluid prevents the lumens of the conduits 20, 24 and 26 from sticking together and closing while being sterilized. The presence of the portion of the fluid F thus makes it possible to sterilize the set 16, which could be formed completely of vinyl plastic, by means of autoclaving simultaneously with sterilization of the container 12 and the fluid F. When the assembly 10 is removed from the autoclave, the connector 40 has become permanently bonded to the port 14. The assembly 10 is then a single sterile unit which can be packaged for subsequent delivery.

The fused bond between the connector 40 and the port 14 eliminates any need to use a liquid solvent to bond the set to the container. Hence, there is no solvent residue present which can leach into the fluid F in the container 12. Prior to autoclaving, the container 12, the fluid F and the set 17 can be non-sterile. After autoclaving, the unitary assembly 10, including the fluid F, is sterile.

FIGS. 5A through 5D schematically illustrate the present method. FIG. 5A schematically illustrates the container 12 prior to assembly with the set 17. Prior to assembly with the set 17, the container 12 has been partially filled with fluid F. The set 17 is a sealed set except for the connector 40 which is coupled to the conduit 20. FIG. 5B illustrates the container 12 in fluid flow communication with the set 17. FIG. 5C illustrates the assembly 10 being placed in an autoclave A for steam sterilization. FIG. 5D illustrates the unitary assembly 10 after sterilization. In the assembly 10 of FIG. 5D, the connector 40 is permanently bonded to the container 12.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A method of affixing a fluid delivery set to a container of fluid while simultaneously sterilizing the container, the set and the fluid comprising the steps of:

providing a first nonsterile subassembly comprising a fluid-filled container with a sealed, pierceable port, said port being constructed of a unitary composition which softens upon exposure to heat sufficient to sterilize the container and its fluid contents;

providing a second nonsterile subassembly comprising a fluid transfer set with a fluid flow conduit sealed at one end and having at another end a hollow spike connector affixed thereto for piercing the container port, the exterior of the spike connector including a material which is sealingly compatible with the interior material of the port and which softens upon exposure to heat sufficient to sterilize the fluid transfer set;

creating a nonsterile assemblage of the first and second subassemblies by inserting the spike connector into the pierceable port to break the seal permitting fluid to flow from the container into the set toward the closed end thereof; and exposing the nonsterile assemblage to heat sufficient to sterilize the container, the fluid transfer set, and the fluid, thereby softening the interior of the port and the exterior of the spike connector to fuse the spike exterior directly with the port interior, thereby bonding the transfer set to the container while simultaneously sterilizing the formerly nonsterile assemblage.

* * * * *